(12) United States Patent
Bauer et al.

(10) Patent No.: US 11,861,164 B2
(45) Date of Patent: Jan. 2, 2024

(54) INTERFACE FOR A MEDICAL DEVICE WITH AN ADAPTIVE ACTUATION SENSOR

(71) Applicant: B. Braun Avitum AG, Melsungen (DE)

(72) Inventors: Florian Bauer, Melsungen (DE); Christian Schleicher, Dipperz (DE)

(73) Assignee: B. Braun Avitum AG, Melsungen (DE)

( * ) Notice: Subject to any disclaimer, the term of this patent is extended or adjusted under 35 U.S.C. 154(b) by 58 days.

(21) Appl. No.: 17/633,288

(22) PCT Filed: Aug. 13, 2020

(86) PCT No.: PCT/EP2020/072758
§ 371 (c)(1),
(2) Date: Feb. 7, 2022

(87) PCT Pub. No.: WO2021/028535
PCT Pub. Date: Feb. 18, 2021

(65) Prior Publication Data
US 2022/0365674 A1 Nov. 17, 2022

(30) Foreign Application Priority Data
Aug. 13, 2019 (DE) .................... 10 2019 121 843.8

(51) Int. Cl.
*G06F 3/041* (2006.01)
*G06F 3/042* (2006.01)
(Continued)

(52) U.S. Cl.
CPC ....... *G06F 3/04886* (2013.01); *A61M 1/1601* (2014.02); *G06F 3/042* (2013.01);
(Continued)

(58) Field of Classification Search
CPC .... G06F 3/0428; G06F 3/04886; G06F 3/042; G06F 3/0416; G06F 3/044; G06F 3/017;
(Continued)

(56) References Cited

U.S. PATENT DOCUMENTS

| 5,788,851 A | 8/1998 | Kenley et al. |
| 2004/0130576 A1* | 7/2004 | Fujita ............. G06F 3/04886 715/781 |

(Continued)

FOREIGN PATENT DOCUMENTS

| AT | 12382 U1 | 4/2012 |
| BE | 1022014 B1 | 2/2016 |

(Continued)

OTHER PUBLICATIONS

Written Opinion received in International Application No. PCT/EP2020/072758 dated Nov. 18, 2020, with translation, 10 pages.

(Continued)

*Primary Examiner* — Ryan A Lubit
(74) *Attorney, Agent, or Firm* — Christopher A. Rothe; Culhane Meadows, PLLC

(57) ABSTRACT

An interface for a medical device, in particular an extracorporeal blood treatment machine or a dialysis machine, includes a display for displaying display operating elements, base operating elements provided next to the display, and an optical actuation sensor. The optical actuation sensor detects a user interaction with, in particular a touching of, the display operating elements of the display and the base operating elements disposed in the same plane. The optical actuation sensor can be partially activated or deactivated.

13 Claims, 1 Drawing Sheet

(51) Int. Cl.
*G06F 3/044* (2006.01)
*G06F 3/04886* (2022.01)
*A61M 1/16* (2006.01)

(52) U.S. Cl.
CPC ............ *G06F 3/044* (2013.01); *G06F 3/0416* (2013.01); *A61M 2205/505* (2013.01); *G06F 2203/04108* (2013.01)

(58) Field of Classification Search
CPC .. G06F 3/04883; G06F 1/1616; G06F 1/1643; G06F 1/169; G06F 2203/04106; G06F 2203/04108; A61M 1/14; A61M 1/1601; A61M 1/36; A61M 2205/505
See application file for complete search history.

(56) References Cited

U.S. PATENT DOCUMENTS

| | | | | |
|---|---|---|---|---|
| 2010/0177049 A1* | 7/2010 | Levy | ............... | G06F 3/0488 345/173 |
| 2011/0063254 A1 | 3/2011 | Chou et al. | | |
| 2011/0285669 A1* | 11/2011 | Lassesson | ............ | G06F 3/0428 345/175 |
| 2012/0044143 A1* | 2/2012 | Newton | ............... | G06F 1/1616 345/161 |
| 2012/0212434 A1 | 8/2012 | Bluemler et al. | | |
| 2013/0202488 A1 | 8/2013 | Langer et al. | | |
| 2017/0242491 A1 | 8/2017 | Wild et al. | | |
| 2018/0015215 A1 | 1/2018 | Peters et al. | | |
| 2018/0136788 A1* | 5/2018 | He | ............... | G06F 3/042 |
| 2018/0335892 A1 | 11/2018 | Lakshmireddy | | |

FOREIGN PATENT DOCUMENTS

| | | |
|---|---|---|
| DE | 3517686 A1 | 11/1986 |
| DE | 102010064056 A1 | 6/2012 |
| DE | 102011075751 A1 | 11/2012 |
| DE | 102011106786 A1 | 1/2013 |
| DE | 102014202834 A1 | 9/2015 |
| DE | 102016112886 A1 | 1/2018 |
| EP | 1308410 A1 | 5/2003 |
| EP | 1698360 A1 | 9/2006 |
| EP | 2315103 A2 | 4/2011 |
| JP | 2011033720 A | 2/2011 |
| WO | 2010110683 A2 | 9/2010 |

OTHER PUBLICATIONS

Search Report received in German Application No. 10 2019 121 843.8 dated Jul. 22, 2020, with translation, 16 pages.
Search Report received in International Application No. PCT/EP2020/072758 dated Nov. 18, 2020, with translation, 7 pages.

* cited by examiner

INTERFACE FOR A MEDICAL DEVICE WITH AN ADAPTIVE ACTUATION SENSOR

CROSS-REFERENCES TO RELATED APPLICATIONS

This application is the United States national phase entry of International Application No. PCT/EP2020/072758, filed Aug. 13, 2020, and claims priority to German Application No. 10 2019 121 843.8, filed Aug. 13, 2019. The contents of International Application No. PCT/EP2020/072758 and German Application No. 10 2019 121 843.8 are incorporated by reference herein in their entireties.

FIELD

The present invention relates to an interface for a medical device, in particular an extracorporeal blood treatment machine or a dialysis machine, comprising a display for displaying display operating elements and base operating elements, which are provided next to the display.

BACKGROUND

Medical devices, in particular extracorporeal blood treatment machines or dialysis machines, include display devices and input elements, hereinafter also referred to as interfaces, which are required to output information and to be operated by the user. Said interfaces are subject to versatile requirements and constraints, in particular regarding the operating safety and the disinfecting capability.

For example, there are medical devices including, for safe operation of important components of the machine/the medical device, a strip with various hardware push buttons beneath a monitor. Said buttons comprise, for example, a power button, an enter button, a start/stop button for the blood pump, an acknowledgment button for incoming alarms as well as a plus button and a minus button. Said keys/buttons must be sealed against biological contamination and, at the same time, must be capable of tolerating aggressive disinfectants. This can be realized by choosing push buttons which already meet these requirements, or they are protected by an appropriate disinfectable film. For example, a front panel is provided in which push buttons are used that are disposed behind a sealed plastic film. The film is semi-transparent at the positions of the buttons to be able to highlight the buttons by integrated LEDs. Further, such a machine can be operated by means of a resistive touch display. The latter is embedded in the case and is also protected by a disinfectable film. Leakages occurring when the plastic film is attached may allow chemical and biological substances to reach behind the film and to possibly damage or block the push buttons/the touch screen.

Several competitive products make use of such a solution for their front panel, for example. Apart from the buttons, separate places are provided for status LEDs. The main operating panel in all machines is a (capacitive or resistive) touch display embedded in the case. The touch functionality is directly connected to the display function.

It is a drawback that the functioning of the embedded display may be faulty when it is heavily stained. In a gap between the case and the display, liquid may tend to collect and get stuck, which impedes cleaning and disinfection and moreover may possibly result in a defect of the display. In the event of a defect of the display, these machines can be operated only via the afore-mentioned push buttons. Consequently, a defect of the display presentation entails complete deactivation of the touch functionalities and results in a complicated and patient-unfriendly completion of therapy. It is another drawback of a touch display that operating the same with gloves possibly cannot be detected.

It is also a drawback of the previous devices that push buttons are mechanical components which therefore are also subject to mechanical wear. This applies mutatis mutandis to a resistive touch function which (due to touching) is exposed to physical strain. Touch displays may wear out over time and while in active use, developing imprint marks and even touch recognition errors. Incorrect or even ruthless operation of the buttons and/or the touch display may damage the same, thus requiring replacement of the complete front panel. Furthermore, assembly or replacement of such front panel or interface is complex, as plural subassemblies (e.g., electro-mechanical subassemblies, LEDs, button cases, the cover film, resistive touch function elements and the display) must be utilized/mounted during assembly. In addition, electrical switches must be debounced on the hardware and/or software side. Buttons that are already debounced are expensive, among other things.

Moreover, it is known from DE 10 2016 112 886 A1, for example, to provide a projection surface of a dialysis machine which can be spotlighted by a projector and includes interaction elements to be projected thereto, wherein the interaction elements can be actuated via two channels, for example, via a first position detection system with an ultrasonic unit and a touch sensor technology on the projection surface as well as via a second position detection system with an infrared scanning and a 3D camera. This system, too, shows a plurality of problems. For example, the fail-safety is not ensured, as, e.g., when the projector fails, the dialysis machine can possibly no longer be operated safely. Further, the individual actuating elements are subjected to wear and potential damage by a user. In addition, cleaning of the entire system is impeded, inter alia, because the projector and the attachment thereof produce new edges and interfaces that are difficult to clean.

SUMMARY

It is the object underlying the present invention to improve or eliminate drawbacks of the state of the art. In particular, an interface for a medical device is to be provided which is fail-safe and/or difficult to damage and/or easy to operate and/or easy to clean.

More precisely, the object underlying the invention is achieved by an interface for a medical device, particularly an extracorporeal blood treatment machine or a dialysis machine, comprising a display for displaying display operating elements, base operating elements which are provided next to the display, and an optical actuation sensor or actuation sensor technology which is designed to detect a user interaction with, in particular a touching of, the display operating elements of the display and the base operating elements disposed in the same plane, and which can be partially activated or deactivated/which is configured to be partially activated or deactivated. That is to say, the actuation sensor (also referred to as sensor) is intended and designed to specifically detect in regions and/or stop in regions the detection of the user interaction with the display operating elements and the base operating elements, or in other words, to ignore the interaction in particular regions of the interface. The actuation sensor monitors both a region of the display and a region next to the display on which the base operating elements are arranged, and (optionally) detects user interactions in the monitored regions.

Consequently, it is the basic idea of the present invention that, by using a positioning sensor (as touch element) in combination with a typical indicating display, mechanical loads, faulty or wearing components, possible leakages by faulty assembly as well as problems when disinfecting the monitor/interface are to be avoided. The optical and adaptively switchable positioning sensor/actuation sensor for smooth surfaces enables touch or proximity detection on any smooth surface without necessarily having to touch the latter directly.

In other words, the object is achieved by an interface with an optical actuation sensor (sensor device) or an optical touch/proximity sensor technology and a number of operating elements provided on and next to a display (in particular a display without a touch sensor technology integrated in the display surface), the operating elements being monitored optionally and preferably independently of each other by the optical actuation sensor to monitor particular regions or operating elements depending on the therapy or the situation and to detect actuation thereof. Or, in yet other words, an adaptive purely optical actuation sensor can prevent particular, optionally deactivated input surfaces or operating elements from being actuated, or, on the other hand, can permit actuation of particular, optionally activated input surfaces or operating elements, if they are required.

Preferably, the interface includes a controller that compares the data of the optical actuation sensor and, if necessary, additionally provided sensors to information regarding a position of the display and base operating elements to evaluate or recognize an input of a user. The positions of the operating elements, in particular of the base operating elements, can be deposited as fixed location data (position data/data regarding a fixed position of the operating elements on the medical device or the interface) in a memory of the controller. Alternatively, or additionally, the positions of the display operating elements can be compared to data of a display control, when a user's actuation is detected in the region of the display by the optical actuation sensor. The capability of being partially activated and deactivated can also be controlled by the controller, either by directly switching on and off parts of the optical actuation sensor/sensor technology, which is particularly energy-saving, or by evaluating only parts of the data detected by the optical actuation sensor/sensor technology, which possibly allows for a more precise measurement/detection.

The optical actuation sensor may utilize any technology which is sufficiently precise and is suitable for touching or proximity detection on a flat or planar detection surface. The sensor is particularly a contactless functioning sensor. It is useful when the sensor is provided as an element separate/formed separately from the display and/or the operating elements (i.e., is not integrated in the display and/or the operating elements). That is to say, the sensor preferably monitors a region directly ahead of the display and the operating elements. Components of the sensor are preferably arranged next to or in the vicinity of the display and the operating elements/the interface, or in other words, do not superimpose the latter, so that a user does not touch/does not just inadvertently happen to touch the components of the sensor when he/she operates the display and the operating elements. For example, components of the sensor may be arranged on the side of and/or above and/or beneath the display and the operating elements. Preferably, components of the sensor, e.g., an emitter and a dedicated receiver, are arranged on opposite sides of the display and the operating elements.

The base operating elements can provide functional surfaces at the edges of the interface and, resp., around the display. Said functional surfaces can fulfill general operating functions, for example, such as an on/off switch (power button), an input acknowledgment switch (enter button) and a plus/minus switch, or basic functions which are required for each medical device of this type. Using the example of a dialysis machine, this may be a start/stop switch for a blood pump and/or an acknowledgment switch for incoming alarms (acknowledgment or switch-off of the alarm). Further, a small mousepad or (quick) function switches/buttons may be provided, e.g., for connecting or blocking a bypass, disconnecting a patient or emptying a bicarbonate cartridge. The base operating elements can be positioned at almost any position (in the vicinity of the display). For example, the fact that known push buttons can be dispensed with, as an actuation of the base operating elements is detected by the optical actuation sensor, advantageously allows to assemble or, in the case of damage, to replace fewer components.

It is further advantageous that, instead of a (capacitive or resistive) touch display as it is used in the state of the art, a typical indicating display (which has no touch functionality) can be used to which a user does not have to apply unnecessary pressure and which is thus subjected to less wear and a lower probability of being damaged. As a result, an inexpensive robust display can be chosen. In other words, saving concerning the display (monitor) is possible as no touch display but a typical indicating display can be used. Furthermore, an operation with gloves, which would be difficult for a touch display, is easily possible for the interface according to the invention. The touch function and the display are thus separated for better robustness and fault recognition.

It is another advantage that the problems of the known afore-described devices can be avoided according to which, when the display fails, the touch function would either be still active, which would represent a non-allowed operability without visual feedback, or according to which the touch would be completely deactivated, which would restrict the operability to the electro-mechanical push elements. Instead, according to the present invention, when the display fails, the touch/proximity functionality (touch functionality) provided by the optical actuation sensor can be adapted to the present situation, and more precisely restricted to the functioning parts of the interface, thereby continuing to ensure operability.

Accordingly, to sum up, the present invention provides a robust fail-safe touch recognition by an optical actuation sensor module/optical actuation sensor which is functional on all smooth surfaces.

Preferably, the display operating elements or the display as well as the base operating elements can be adaptively wired separately or in groups by partially activating or deactivating the optical actuation sensor. In other words, the optical actuation sensor that monitors the interface surface with respect to an actuation by a user can fade out particular interface subareas and, in this way, ignore a user interaction with one of said subareas. That is to say, different operating zones can be adaptively switched on and off on the complete monitor surface. Therefore, the probability of misuse by a user can be reduced. For example, for a parameter input, the optical actuation sensor can be deactivated for all regions except the fields required for this input so that a user cannot continue to operate the device without entering said parameters. Furthermore, specific operating elements can be added as needed, thus guaranteeing redundant safety. In this way, for example, operating functionalities are guaranteed, if one of the (three) monitor components (optical actuation sensor, display and a capacitive proximity sensor described in detail below) fails.

This is advantageous, for example, when the optical actuation sensor is designed to be capable of being deactivated in the case of an at least partial failure of the display in the region of the display or a respective subregion. In this way, a user can be prevented from making inputs on the display which is no longer working correctly. That is, providing an adaptive activation capability and deactivation capability and/or the possibility to ignore/deactivate specific parts of the region monitored by the optical actuation sensor serves for securing the functionality of the interface and enables the medial device to be still safely operated even if the display fails.

Furthermore, the medical device can be designed to be operable only by the base operating elements and without the display at least such that a current therapy can be completed safely and preferably regularly. This is of particular advantage as in this way the medical device is still sufficiently operable, even if the display fails or is defective, to complete a therapy in a manner which does not or only slightly impair or disturb the patient.

Of preference, the optical actuation sensor has a sensor panel/sensor plane/sensor surface in parallel to the display and the base operating elements which extends so that a detection surface spanned by the actuation sensor superimposes the display and the base operating elements, in particular covers the latter on a side of the display and the base operating elements facing the user/is located in parallel thereto above the display and the base operating elements. In particular, a length of the sensor panel can correspond at least to an expansion of the display and the base operating elements and can preferably correspond to the entire length of the interface. Further preferred, the sensor panel covers the entire interface.

For this purpose, a detection surface which is checked for interruptions by plural sensors within the same module over the entire surface beneath the sensor module via plural optical emitters. For example, an infrared surface or detection surface provided/spanned by infrared emitters (as part of the optical actuation sensor according to one configuration variant) can be used. Should an object or finger interrupt the surface, the module (the optical actuation sensor) determines the accurate position, shape and direction of movement. These position data can then be interpreted and traced back to deposited functions (touch recognized).

According to one aspect of the invention, the base operating elements or front panel elements are two-dimensional markers, in particular prints or stickers, on a case portion of the medical device which have no mechanical or electrical components per se. In other words, the front panel elements can be realized by simple prints, in particular without any further (exposed) electronics and/or mechanics. Also, a lasered or etched marker is imaginable. That is to say, the base operating elements per se with which a user interacts and which might be exposed to environmental influences such as disinfectants, germs, or the like, have substantially the same stability as the case portion itself and a protective film can be dispensed with. This is possible, inter alia, by the fact that an optical actuation sensor is provided which, for detecting an actuation of the base operating elements, merely requires a line of sight toward the same. Alternatively, or additionally, this is enabled by the fact that capacitive proximity sensors, as will be described in detail in the following, are arranged behind the respective markers. Should the print or sticker forming the marker/base operating element and/or the colors thereof be worn out and be no longer clearly recognizable, it is of advantage when these prints or stickers are configured to be renewable in a simple manner, in particular without having to replace the entire case portion.

It is further preferred that capacitive proximity sensors which are operated or connected in parallel to the actuation sensor or, particularly in the case of failure of the same, instead of the actuation sensor, are arranged behind the base operating elements. In other words, the front panel elements can be expanded, as a redundant measure, by capacitive touch surfaces so as to ensure an extended operability in the event of possible component failures.

The capacitive proximity sensors are based, for example, on sensor technology marketed under the trademark CAPSENSE™ ("capacitive sensing"/capacitive sensor technology) which allows to recognize proximities and touching without any mechanical components. To this end, on a printed circuit board, one or more touch/push surfaces are provided and appropriately wired so that a specific capacity adjusts on the same (the printed circuit board or the at least one push surface). To this end, the push surface is divided into two or more portions so that the desired capacity can adjust between the portions. If an object or a body part is moved to the vicinity of the push surface, the capacity between the portions will change. This change can be recorded and interpreted by an appropriate micro-controller, such as micro-controller marketed under the trademark CAPSENSE™-IC. In this way, keystrokes up to movement patterns such as swipes can be recognized or even operating elements similar to mousepads can be realized.

The advantage of the interface according to the invention is that (for the base operating elements) no electro-mechanical subassemblies are required for a keystroke. Merely a simple integration (of the capacitive proximity sensors for the base operating elements/buttons) has to be provided on a usually already existing front panel printed board. Only a footprint on the PCT (printed circuit board) as well as a matching controller are required to integrate all capacitive operating elements. Safe recognition of a keystroke (or of a key touch or approximation) is possible and there is no necessity of a mechanical debouncing. The key functions can be easily extended via the controller used and can be individually adapted/assigned, where necessary. It may be provided (in addition to the simple actuation recognition) also an expansion for the movement recognition of sliding and rotational movements (small touchpad).

The capacitive proximity sensors/elements, such as elements marketed under the trademark CAPSENSE™, may serve as a redundant safety feature, should the sensor module/the optical actuation sensor have a defect. For example, via a mousepad, such as a mousepad marketed under the trademark CAPSENSE™, an operability which is somewhat restricted but still covers everything (all substantial functions) can be ensured. In the event of a display defect, the touch functionality of the sensor module/optical actuation sensor can be deactivated for this region (i.e., for the region of the display), and, if necessary, a therapy can still be regulated and completed sufficiently via auxiliary keys at the edge of the monitor. Alternatively, or additionally, in the event of a failure of the elements/the capacitive proximity sensors, the operability can be continued to be given/ensured via the sensor module. Sensor surfaces (i.e., parts of the detection surface of the optical actuation sensor) for the auxiliary keys and the mousepad (base operating elements) can be adaptively connected only in the case of a defective display and otherwise can be deactivated by the sensor module. Alternatively, the base operating elements can be activated in parallel to the display operating elements so that the user can decide how he/she preferably operates the medical device. Alternatively, or additionally, in the case of failure of the optical actuation sensor, the medical device and, resp., a therapy carried out by the same can be controlled via the capacitive proximity sensors. This is still possible even if moreover the display has also failed. Summing up, the present invention provides a multi-stage redundance by replacing the display input and by replacing the optical position recognition.

Another aspect of the invention relates to a preferably rigid safety shield which is provided such that it extends over a region of the interface including the display. Preferably, the safety shield is located/extends over a region of the whole interface, i.e., over the whole surface of the interface, and further preferred is located completely over a case portion of the medical device on which the interface is provided.

In other words, the (indicating) display can be installed behind a safety shield, in particular a plexiglass or glass shield. It is of particular advantage when the safety shield is a plastic plate made of a rigid material. As the safety shield is a rigid shield, it can be mounted more easily and, in contrast to a film known from the state of the art, no folds or cracks can form during assembly. Furthermore, the safety shield is less susceptible to wear, as it is more stable than a film known from the state of the art and, moreover, in contrast to said film, is not exposed to pressure or movements, as would be experienced by the film when the operating elements covered by said film in the form of mechanical push buttons are actuated. A smooth/flat plastic material/glass can be properly disinfected. Further, a plastic material can be chosen that is resistant to aggressive disinfectants. The safety shield serves for protecting the display against damage, such as by those disinfectants, and against staining. The safety shield equally prevents, when it extends also over the base operating elements, the respective prints or stickers from being worn out by frequent touching by the user.

Moreover, there are no possibilities for leakages or the latter can be avoided at least largely, in particular when the safety shield completely covers the interface or the entire case portion and ends/is aligned with a rim or edge of the case. I.e., there are no mounting gaps or edges/cuttings/grooves/corners which would constitute possible leakages and regions that are difficult to disinfect, where liquids, for example, might penetrate. Where necessary, moreover wear of the push surfaces (base operating elements and related capacitive proximity sensors) can be prevented, as said push surfaces are only copper footprints behind the stable safety shield or plastic plate. To sum up, it is noted that the selection and the interaction of the sensor technology of the present invention enables to provide a robust, easy-to-mount and easy-to-disinfect cover or protection for the display and/or base operating elements.

According to another advantageous aspect of the invention, at least one indicator device is provided, in particular in the form of vibration elements and/or LEDs, which give the user feedback, particularly haptic and/or optical feedback, about inputs made and/or reports of the medical device.

In other words, haptic feedback can be integrated via additional vibration and/or optical signaling. In this case, small vibration cells are disposed behind or next to the safety shield (glass or plastic plate), or possibly also LEDs are provided behind or next to the front panel elements (base operating elements) for optical feedback. In this way, even if the display fails, a user still gets feedback about his/her inputs made by means of the base operating elements. For example, a state of the medical device being ready to initiate the next treatment step can be indicated by a green LED and, on the other hand, a faulty input can be signaled by a red LED and/or vibration of the interface. Alternatively, or additionally, a loudspeaker may be provided as indicator device.

In addition, the object underlying the invention is achieved by a medical device, in particular an extracorporeal blood treatment machine or dialysis machine, comprising an afore-described interface.

In other words, the object underlying the invention is achieved by using, instead of front panel push buttons and a touch display provided in state-of-the-art dialysis machines, an optical and adaptive actuation sensor which enables to exactly position and recognize gestures of a finger or an object as well as the shape thereof on any smooth surface. The optical actuation sensor (the sensor module) can make use of any current technology, if it ensures precise detection for an optical and flat sensor surface and can be adaptively wired. In the current state of the art, neither an adaptively variable touch sensor surface nor a multi-stage redundance in the case of failure is described. The idea of the present invention consists in using an optical surface for the touch detection which covers the entire monitor and can be adaptively deactivated or activated for specific regions. In the case of failure of the display, the operating functionality could be deactivated for the region of the display surface without affecting front panel elements or extended operating fields at the edge of the case (i.e., base operating elements). Further, the redundance of the capacitive (base) operating elements can help ensure restricted but still sufficient operability of the machine, even if the sensor module fails. Summing up, if the display or the touch element fails, accompanying failure of the respective other component can be avoided and redundance (by IR and sensors such as sensors marketed under the trademark CAPSENSE™) is ensured with safety-relevant operating elements of the front panel. Such adaptive and redundant operating concept which can be applied without any mechanical influences and to any smooth surfaces does not exist in the current state of the art.

In yet other words, the present invention is based on a monitor concept (interface) including an afore-described optical sensor module (optical actuation sensor) which covers the complete monitor front (the complete interface). Any conventional display technology may be used as display. Front panel elements and possibly further functional surfaces (i.e., base operating elements), which are arranged as electro-mechanical operating buttons in common dialysis machines, according to the present invention are printed as symbols preferably onto the monitor front (or the case portion on which the interface/monitor concept is arranged) and are equally recognized via the sensor module. In order to guarantee operability if the sensor module fails, said elements can be backed via a capacity touch sensor (for example, sensor technology marketed under the trademark CAPSENSE™) behind the printed surface. The attached sensor module is capable of recognizing touch functionalities on the display surface and on the surrounding operating elements printed and backed by sensor technology marketed under the trademark CAPSENSE™ and also of implementing/processing the same. In so doing, the touch function can be switched off and on adaptively for different monitor regions. In this way, auxiliary keys or mousepads (i.e., base operating elements) or else the touch functionality of the display (i.e., display operating elements) can be wired separately and adaptively. A smooth and robust plastic or glass plate which is resistant to chemicals and is easy to disinfect may be placed over the complete monitor front.

BRIEF DESCRIPTION OF THE DRAWING FIGURES

In the following, the present invention shall be described by means of a preferred embodiment. This embodiment is only illustrative, however, and is not intended to limit the scope of protection of the present invention.

DETAILED DESCRIPTION

Figure 1:
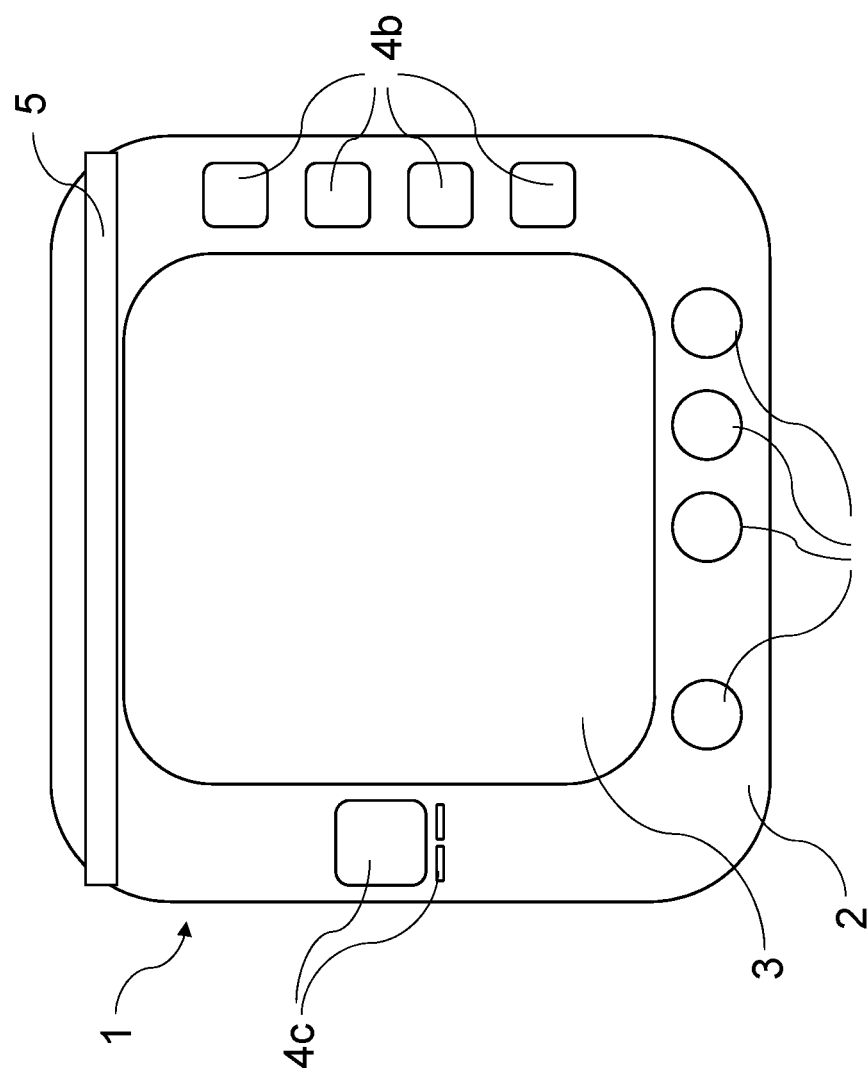
FIG. 1 shows a schematic top view onto an interface according to the invention as set forth in an embodiment of the invention.

An interface 1 according to the present invention shown frontally in FIG. 1 is arranged on a case portion 2, in particular a front panel, of a dialysis machine. The interface 1 includes a display 3 which is provided to present treatment-specific information and input surfaces or display operating elements. In the vicinity of the (directly adjacent) display 3, base operating elements 4a, 4b, 4c (hereinafter referred to as buttons) are shown. In this embodiment, these are examples of first buttons 4a which are arranged below the display 3 and operate, e.g., basic functions such as switch on and off, acknowledge/enter, etc., second buttons 4b which are arranged on the right of the display 3 and serve as quick-function buttons for functions such as "bypass", "disconnect patient", "empty cartridge", etc., as well as third buttons 4c which are arranged on the left of the display 3 and serve as mousepad. Said buttons 4a, 4b, 4c are markers printed or glued onto the housing portion 2 on which the interface 1 is arranged, said markers characterizing additional input surfaces for operating the dialysis machine.

Furthermore, a sensor panel 5 is arranged next to, in this embodiment above, the display 3. Said sensor panel 5 extends in parallel to an edge of the display 3 and has a length that corresponds at least to the length of the display 3 and the adjacent buttons 4c, 4b. That is to say, the sensor panel 5 extends so that both the display 3 and the display operating elements possibly indicated thereon as well as the buttons 4a, 4b, 4c are located on the side of the sensor panel 5 and can be detected by the same. Optical sensors, in particular infrared sensors and/or emitters, provided in one side of the sensor panel 5 are aligned in the direction of the display 3 and the buttons 4a, 4b, 4c and span a detection surface 6 that extends both over the display 3 in parallel thereto and over the buttons 4a, 4b, 4c. Thus, the sensor panel 5 can detect when a user passes through the detection surface 6 and at which position this takes place so as to touch one of the display operating elements of the display 3 or one of the buttons 4a, 4b, 4c and, thus, to operate the interface 3. Accordingly, by comparing the measuring data of the sensor panel 5 to the known or set positions of the display operating elements and buttons 4a, 4b, 4c a control of the dialysis machine can be performed.

Figure 2:
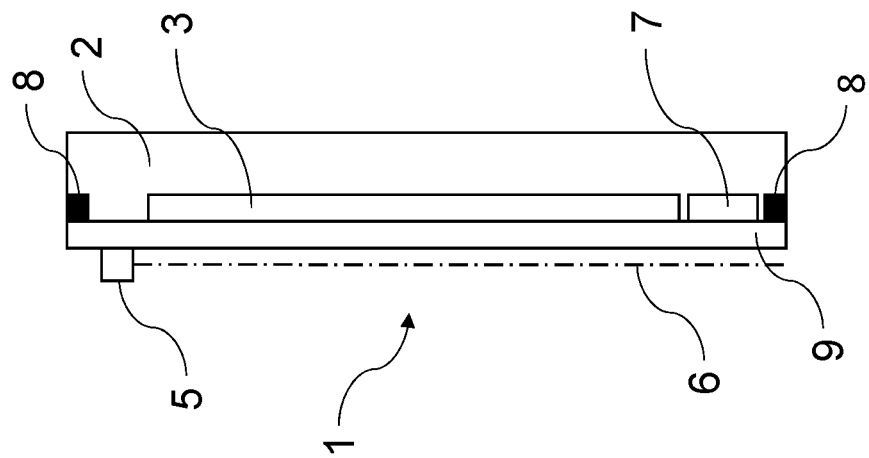
FIG. 2 shows a schematic cross-sectional view of the interface as set forth in the embodiment.

FIG. 2 is a schematic cross-sectional view of the interface 1 and illustrates the structure thereof. As afore-described, the display 3 is arranged or embedded on a front side of the case portion 2. Beneath the display 3, the buttons 4a, 4b, 4c are glued or printed onto the case portion 2, but they are not visible in this view due to their two-dimensional configuration. Behind the buttons 4a, 4b, 4c, capacitive touch sensors 7 which serve as redundant sensors to detect touching or operations of the buttons by a user are arranged in the case portion 2. Further, above the display 3 and beneath the buttons 4a, 4b, 4c, indicator devices 8, in particular vibration elements and/or LEDs, are arranged on or embedded at the case portion 2. They may provide a user with haptic and/or optical feedback in the case of specific inputs or reports.

The case portion 2 that includes the interface 1 is completely covered by a safety shield 9, preferably made of Plexiglass. Said safety shield 9 prevents the display 3 and the buttons 4 from being stained, prevents the latter from being worn out or damaged by a user's touching, aggressive disinfectants, etc., and moreover protects them against application of excessive force. Such safety shield 9 is stable and, in addition, can be attached and cleaned easily and quickly, in particular because it completely covers the case portion 2.

As already described in the foregoing, the sensor panel 5 is further arranged above the display 3 on a front face of the safety shield 9 in such a way that a detection field 6 extending directly next to and in parallel to the safety shield 9 and extending both over the display 3 and over the buttons 4a, 4b, 4c is spanned by the optical sensors/emitters disposed in the sensor panel 5.

In other words, the Figures illustrate a possible configuration variant of the adaptive monitor concept. The display 3 and the operating elements 4a, 4b, 4c are realized in printed form on the monitor case 2 and as elements 7 behind the monitor case 2, for example elements marketed under the trademark CAPSENSE™. The safety shield, in particular a Plexiglass pane 9, is placed over the complete monitor front on which the sensor module 5 is installed. The latter places an optical sensor surface 6 which can detect elements as well as the movement and shape thereof, if they interrupt the sensor surface 6, over the monitor front. Haptic feedback can be made possible, e.g., via vibration elements (indicator devices) 8 behind the safety shield/Plexiglass plate 9.

During normal operation, in this way the complete monitor front can be operated via the optical sensor module 5. Auxiliary functionalities such as the mousepad 4c or the quick-function buttons 4b may be switched to be inactive and are ignored by the sensor surface 6. In the event of a defective display, the touch functionalities of the display surface 3 can be deactivated and those of the auxiliary keys 4a, 4b, 4c can be activated to be able to complete the treatment of the patient in a safe and largely comfortable manner. Accordingly, the sensor surface 6 would evaluate only contacts outside the display area 3. Should sensor module 5 fail, an operation by the auxiliary keys 4a, 4b, 4c is also still safeguarded, as now the functionalities can be activated. This means that the machine, similarly to a laptop, can still be transferred to a safe state via the mousepad 4c largely easily without having to initiate emergency measures. These touch surfaces 6 which can be wired adaptively and redundantly help develop a robust and innovative operating concept which is easy to clean and can be precisely operated even with gloves or by objects.

The invention claimed is:

1. An interface for a medical device, the interface comprising:
    a display;
    operating buttons which are provided next to the display; and
    at least one optical actuation sensor which detects user interaction with the icons and the operating buttons, the at least one optical actuation sensor configured for at least one of:
adaptively switching different parts of the actuation zones on and off, and
omitting a partial area of the display to ignore user interaction with the partial area of the display,
wherein the at least one optical actuation sensor is configured to be deactivated, when the display at least partially fails, in an area of the display or in a respective partial area thereof.

2. The interface according to claim 1, wherein the at least one optical actuation sensor comprises a sensor panel extending in parallel to the display and the operating buttons so that a detection surface spanned by the at least one optical actuation sensor superimposes the display and the operating buttons.

3. The interface according to claim 2, wherein a length of the sensor panel corresponds at least to an extension of the display and the operating buttons.

4. The interface according to claim 1, further comprising capacitive proximity sensors arranged behind the operating buttons, the capacitive proximity sensors being operated or connected in parallel to the at least one optical actuation sensor.

5. The interface according to claim 1, further comprising a safety shield that extends over an area of the interface including the display.

6. The interface according to claim 1, further comprising at least one indicator device configured to provide a user with feedback via inputs made and/or reports of the medical device.

7. A medical device comprising the interface according to claim 1.

8. An interface for a medical device, the interface comprising:
a display;
operating buttons which are provided next to the display; and
at least one optical actuation sensor which detects user interaction with the icons and the operating buttons,
the at least one optical actuation sensor configured for at least one of:
adaptively switching different parts of the actuation zones on and off, and
omitting a partial area of the display to ignore user interaction with the partial area of the display,
wherein the operating buttons allow input to the medical device to keep the medical device operable without the display at least such that a current therapy can be safely and regularly completed.

9. The interface according to claim 8, wherein the operating buttons are two-dimensional markers on a case portion of the medical device.

10. The interface according to claim 8, further comprising capacitive proximity sensors arranged behind the operating buttons, the capacitive proximity sensors being operated or connected in parallel to the at least one optical actuation sensor.

11. The interface according to claim 8, further comprising a safety shield that extends over an area of the interface including the display.

12. The interface according to claim 8, further comprising at least one indicator device configured to provide a user with feedback via inputs made and/or reports of the medical device.

13. A medical device comprising the interface according to claim 8.

* * * * *